United States Patent [19]

Kreis et al.

[11] 4,276,252

[45] Jun. 30, 1981

[54] ADDITION OF SI-BONDED HYDROGEN TO AN ALIPHATIC MULTIPLE BOND

[75] Inventors: Gerhard Kreis, Munich; Karl-Heinrich Wegehaupt, Burghausen, both of Fed. Rep. of Germany

[73] Assignee: Wacker-Chemie GmbH, Munich, Fed. Rep. of Germany

[21] Appl. No.: 85,572

[22] Filed: Oct. 17, 1979

[30] Foreign Application Priority Data

Oct. 26, 1978 [DE] Fed. Rep. of Germany ....... 2846621

[51] Int. Cl.$^3$ .............................................. B29C 1/02
[52] U.S. Cl. .................................... 264/222; 528/15; 528/31; 528/32; 528/901; 264/DIG. 30
[58] Field of Search ................... 528/15, 31, 32, 901; 264/222, DIG. 30

[56] References Cited

U.S. PATENT DOCUMENTS

| | | | |
|---|---|---|---|
| 3,159,662 | 12/1964 | Ashby | 528/15 |
| 3,178,464 | 4/1965 | Pierpoint | 528/15 |
| 3,383,356 | 5/1968 | Nielsen | 528/15 |
| 3,814,730 | 6/1974 | Karstedt | 528/15 |
| 4,177,341 | 12/1979 | Kreis et al. | 528/32 |

*Primary Examiner*—Melvyn I. Marquis

[57] ABSTRACT

Silicon containing compounds having Si-bonded hydrogen are added to an aliphatic multiple bond in the presence of a platinum catalyst selected from the group consisting of platinum compounds of the formula $$(R^1)PtX_2,$$

where $R^1$ represents a cyclic hydrocarbon radical or a substituted cyclic hydrocarbon radical having 2 aliphatic carbon-carbon double bonds, X is the same or different halogen atoms and/or the same or different alkyl radicals, and compounds of the formula $$(R_2SO)(Z)PtY_2$$

where R represents the same or different hydrocarbon radicals or substituted hydrocarbon radicals, Z represents a hydrocarbon having a carbon-carbon double bond and Y represents the same or different halogen atoms.

An example of a platinum compound having the general formula $$(R^1)PtX_2,$$

is dicyclopentadiene-platinum dichloride, while an example of a platinum compound having the general formula $$(R_2SO)(Z)PtY_2$$

is dimethylsulfoxide-ethylene-platinum-(II)-dichloride.

10 Claims, No Drawings

ADDITION OF SI-BONDED HYDROGEN TO AN ALIPHATIC MULTIPLE BOND

The present invention relates to the addition of organosilicon compounds containing silicon bonded hydrogen to compounds containing aliphatic unsaturation and more particularly to a process for adding organosilicon compounds containing silicon bonded hydrogen to a compound having aliphatic unsaturation in the presence of a platinum catalyst.

BACKGROUND OF INVENTION

The addition of organosilicon compounds containing Si-bonded hydrogen to an aliphatic multiple bond is well known and is often referred to as "hydrosilation". Likewise, it is known that hydrosilation can be accelerated with catalyst, such as platinum catalysts. Hydrosilation is further described in U.S. Pat. No. 3,814,730 to Karstedt, in which platinum catalysts are used to effect the addition of an organosilicon compound having a silicon bonded hydrogen atom to an aliphatically unsaturated compound having either olefinic or acetylenic unsaturation and thereby form an adduct having a new silicon carbon linkage.

Compared to the catalysts known heretofore for the addition of Si-bonded hydrogen to an aliphatic multiple bond, the platinum complexes used in this invention have the advantage that they are more effective and/or can be obtained more readily in a pure state from the precipitation reaction and consequently can be diluted to the proper concentration more readily than the conventional platinum catalysts used heretofore.

Therefore, it is an object of this invention to provide a catalyst for effecting the addition of organosilicon compounds containing silicon bonded hydrogen to unsaturated organic compounds. Another object of this invention is to provide a catalyst which is more effective in promoting hydrosilation. Still another object of this invention is to provide a catalyst which is available in substantially pure state and is effective at room temperature. A further object of this invention is to provide a process for promoting the addition of organosilicon compounds having silicon bonded hydrogen to a compound having aliphatic unsaturation.

SUMMARY OF INVENTION

The foregoing objects and others which will become apparent from the following description are accomplished in accordance with this invention, generally speaking, by providing a process for the addition of an organosilicon compound containing Si-bonded hydrogen to a compound having an aliphatic multiple bond in the presence of a platinum catalyst, in which the platinum catalyst is selected from the group consisting of compounds of the formula $(R^1)PtX_2$, where $R^1$ represents a cyclic hydrocarbon radical or a substituted cyclic hydrocarbon radical having two aliphatic carbon-carbon double bonds and X represents the same or different halogen atoms and/or the same or different alkyl radicals; and compounds having the formula $(R_2SO)(Z)PtY_2$, where R represents the same or different hydrocarbon radicals or substituted hydrocarbon radicals, Z is a hydrocarbon having a carbon-carbon double bond and Y represents the same or different halogen atoms.

DETAILED DESCRIPTION OF INVENTION

Examples of cyclic hydrocarbons represented by $R^1$ which have 2 aliphatic carbon-carbon double bonds are dicyclopentadiene and 1,5-cyclooctadiene.

The halogen atoms represented by X are fluorine, chlorine, bromine or iodine atoms, with chlorine being the preferred halogen.

The alkyl radicals represented by X preferably contain from 1 to 4 carbon atoms and are for example the methyl, ethyl, propyl, isopropyl, n-butyl, sec-butyl and tert-butyl radicals.

The preferred platinum complex represented by the formula $(R^1)PtX_2$ is dicyclopentadiene-platinum dichloride, $(C_{10}H_{12})PtCl_2$, since it is very reactive even at room temperature.

Additional examples of platinum complexes having the general formula $(R^1)PtX_2$ are compounds corresponding to the following formulas:

$(C_{10}H_{12})PtBr_2$ $(C_{10}H_{12})PtI_2$ $(C_8H_{12})PtCl_2$ $(C_8H_{12})PtBr_2$ $(C_8H_{12})Pt(CH_3)Cl$ $(C_8H_{12})Pt(CH_3)_2$ $(C_8H_{12})Pt(C_2H_5)_2$ $(C_{10}H_{12})Pt(CH_3)_2$ $(C_{10}H_{12})Pt(C_2H_5)_2$ $(C_{10}H_{12})Pt(C_4H_9)_2$.

In the above formulas "$C_{10}H_{12}$" represents dicyclopentadiene and "$C_8H_{12}$" represents 1,5-cyclooctadiene.

A platinum complex other than the dicyclopentadiene-platinum dichloride is a dicyclopentadiene-platinum complex having $C_1$ to $C_4$-alkyl radicals of the formula

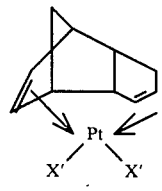

where X' is an alkyl radical having from 1 to 4 carbon atoms.

Platinum complexes of the general formula $$(R^1)PtX_2$$

and their method of preparation are described by J. Chatt et al, Journal of the Chemical Society, 1957, pages 2496 through 2505 and by H. C. Clark et al, Journal of Organometallic Chemistry, 59 (1973), pages 411 through 428.

Dicyclopentadiene-platinum dichloride can be obtained not only by reacting $Na_2PtCl_4 \cdot 4H_2O$ with dicyclopentadiene in n-propanol, but also by reacting $K_2PtCl_4$ with dicyclopentadiene in about 50 percent by weight of aqueous acetic acid. Dicyclopentadiene-platinum dibromide can be obtained by reacting dicyclopentadiene-platinum dichloride with lithium bromide in acetone and dicyclopentadiene-platinum diiodide can be obtained by reacting dicyclopentadiene-platinum dichloride with sodium iodide in acetone.

The substituted radicals represented by R may be aliphatic or aromatic hydrocarbon radicals. It is preferred that they contain from 1 to 10 carbon atoms. The examples cited above for alkyl radicals represented by X are equally applicable to the hydrocarbon radicals represented by R. Additional examples of hydrocarbon radicals represented by R are the phenyl and the benzyl radicals. Examples of substituted hydrocarbon radicals represented by R are the 2-chloroethyl radical, a radical of the formula $—CH_2COOH$, the o-chlorophenyl radical, the o-carboxyphenyl radical and the o-nitrophenyl radical. The radicals represented by R may be connected to form a ring configuration such as occurs in the case of the tetramethylene radical.

The hydrocarbon radicals represented by Z having a carbon-carbon double bond may be linear, branched or cyclic. It is preferred that they contain from 2 to 10 carbon atoms. Examples of hydrocarbon radicals represented by Z are ethylene, propylene, n-1-butene, n-1-pentene, cyclopentene, styrene, cis-2-hexene and 1-nonene.

The halogen atoms represented by Y are fluorine, chlorine, bromine or iodine. Preferably the halogen atoms are chlorine and bromine.

It is preferred that the platinum complex having the following formula $$(R_2SO)(Z)PtY_2$$

be dimethylsulfoxide-ethylene-platinum-(II)-dichloride, $[(CH_3)_2SO](C_2H_4)PtCl_2$, since it is very reactive even at room temperature.

Additional examples of platinum complexes having the general formula $$(R_2SO)(Z)PtY_2$$

are compounds of the following formulas:

$[(CH_3)_2SO](C_3H_6)PtCl_2$ $[(CH_3)_2SO](C_4H_8)PtCl_2$ $[(CH_3)_2SO](C_5H_{10})PtCl_2$ $[(CH_3)_2SO](C_5H_8)PtCl_2$ $[(CH_3)_2SO](C_6H_5CH=CH_2)PtCl_2$ $[(CH_3)_2SO](C_2H_4)PtBr_2$ $[(CH_3)_2SO](C_3H_6)PtBr_2$ $[(C_6H_5)(CH_3)SO](C_2H_4)PtCl_2$ $[(C_6H_5)(CH_3)SO](C_3H_6)PtCl_2$ $[(C_6H_5)(CH_3)SO](C_6H_5CH=CH_2)PtCl_2$ $[(C_6H_5)(CH_3)SO](C_2H_4)PtBr_2$.

In the above formulas "$C_4H_8$" represents n-1-butene and "$C_5H_{10}$" represents n-1-pentene.

Platinum complexes of the following general formula $$(R_2SO)(Z)PtY_2$$

and their preparation are generally known in the art and their preparation is described by H. Boucher et al, Journal of the Chemical Society, Volume 99, 1977, pages 6253 through 6261.

In the sulfoxide-ethylene-platinum-(II)-dihalides, higher boiling hydrocarbons having a carbon-carbon double bond may be substituted for the ethylene.

The amount of platinum catalyst required to promote the addition of a silicon compound containing Si-bonded hydrogen to a compound having an aliphatic multiple bond, may be the same amount of platinum catalyst which have been or could have been used heretofore in the addition of Si-bonded hydrogen to an aliphatic multiple bond. Preferably a sufficient amount of catalyst should be used so that at least $10^{-10}$ gram atom, and more preferably $10^{-8}$ to $10^{-3}$ gram atom of platinum is present, based on elemental platinum, for each gram atom of Si-bonded hydrogen.

The temperature used in the addition process of this invention may be the same as that used or could have been used heretofore in the known processes for the addition of Si-bonded hydrogen to an aliphatic multiple bond in the presence of a platinum catalyst. Thus the temperature ranges from about room temperature up to about 150° C., at atmospheric pressure, i.e., one bar or approximately one bar. However, higher or lower temperatures may be used if desired.

The process of this invention may be used whenever monomeric or polymeric silicon compounds having Si-bonded hydrogen are to be added to monomeric or polymeric compounds having an aliphatic multiple bond. Depending on the compounds which are to be added, other monomeric silicon compounds or dimeric or polymeric, silicon-containing compounds can be prepared or modified by the process of this invention.

Examples of monomeric silicon compounds which may be prepared by the process of this invention are 3-chloropropyltrichlorosilane in which trichlorosilane is reacted with allyl chloride. Also 3-chloropropylmethyldichlorosilane may be prepared by reacting methyldichlorosilane with allyl chloride. Likewise n-propyltrichlorosilane may be prepared by reacting propene with trichlorosilane. Furthermore, methacryloxypropyltrichlorosilane may be prepared by reacting allylmethacrylate with trichlorosilane and vinylmethyldichlorosilane may be prepared by reacting acetylene with methyldichlorosilane.

Examples of dimeric or polymeric silicon containing compounds which may be prepared by the process of this invention are bis-(1,2-trichlorosilyl)-ethane which is prepared by reacting vinyltrichlorosilane with trichlorosilane. Also organosiloxanes having SiC-bonded ester groups are prepared by the addition of at least one diester of allylsuccinic acid to an organosilane having an Si-bonded hydrogen. Likewise the number of aliphatic multiple bonds in polymers may be decreased in, for example, poly-(oxyalkylene)-polyols, by reacting polymers of this type containing aliphatic multiple bonds with organopolysiloxanes having at least two Si-bonded hydrogen atoms per molecule.

Although the process of this invention may be used to modify polymeric silicon-containing compounds, it is equally applicable for crosslinking, i.e., the curing or vulcanization of compositions containing alkenyl groups, especially vinyl groups, and organopolysiloxanes containing Si-bonded hydrogen. In the crosslinking of compositions containing alkenyl groups and organopolysiloxanes containing Si-bonded hydrogen, the activity of the catalyst at room temperature can be of great importance in order to achieve rapid crosslinking at temperatures in the range of from 18° to 35° C. Thus, the process of this invention is preferred for the crosslinking of such compositions which may, for example, be used for potting or encapsulating electrical or electronic devices or which may be used as coatings or as compositions which may be used in preparing coatings which repel adhesive substances, such as for coating paper. Such compositions may also be used for pre-cast concrete molds and for making impressions of human or animal teeth.

In making dental impressions, a mixture containing (a) organopolysiloxanes having silicon bond hydrogen, (b) organopolysiloxanes having aliphatic unsaturation, (c) the platinum catalyst of this invention and (d) other additives, if desired, are applied to the tooth or teeth of which an impression is to be taken and after the material has hardened, the resultant impression is removed from the tooth or teeth.

Agents which retard or inhibit the addition of Si-bonded hydrogen to an aliphatic multiple bond at room temperature may of course be used when necessary or desired. Examples of such retardants are benzotriazole, 1,3-divinyl-1,1,3,3-tetramethyldisiloxane and/or 2-methyl-3-butyn-2-ol.

In the following examples all parts and percentages are by weight unless otherwise specified.

(a) A mixture containing dicyclopentadiene-platinum dichloride and diluent which is used in the examples is prepared in the following manner:

About 0.2 g of dicyclopentadiene-platinum dichloride is dissolved in 20 ml of methylene chloride. The solution is mixed with 100 g of a dimethylpolysiloxane having terminal vinyldimethylsiloxy units and a viscosity of 1000 mPa at 23° C. The mixture is stirred at room temperature and at 1 bar until the methylene chloride evaporates. The resultant mixture contains 0.1 percent of platinum, calculated as elemental platinum.

(b) A mixture containing dimethylsulfoxide-ethylene-platinum-(II)-dichloride and diluent which is used in the following examples is prepared in accordance with the procedure described in (a) above, except that 0.2 g of dimethylsulfoxide-ethylene-platinum-(II)-dichloride is used instead of the 0.2 g of dicyclopentadiene-platinum dichloride. The mixture thus obtained also contains 0.1 percent of platinum, calculated as elemental platinum.

EXAMPLE 1

About 90 g of dimethylpolysiloxane having terminal vinyldimethysiloxy units and a viscosity of 1000 mPa at 23° C., are mixed with 2 g of the platinum complex prepared in accordance with the procedure described in (a) above. The mixture thus obtained is stored for 5 days at room temperature. About 10 g of a copolymer having a viscosity of 700 mPa at 23° C. and containing dimethylsiloxane, methylhydrogensiloxane and trimethylsiloxane units are added to the mixture. The mole ratio of the dimethylsiloxane units to the methylhydrogensiloxane units in the mixture is 1:9. The time which elapsed after the mixing of the copolymer and observable crosslinking of the composition is 2 minutes. The resultant mixture contains about 20 ppm of platinum, calculated as elemental platinum.

EXAMPLE 2

The procedure of Example 1 is repeated, except that 2 g of the platinum complex prepared in accordance with (b) above is substituted for the platinum complex prepared in accordance with (a) above. The organopolysiloxane containing the platinum complex is stored for 5 days before being mixed with the organopolysiloxane containing Si-bonded hydrogen. Crosslinking is observed about 45 seconds after the organopolysiloxane containing the platinum complex is initially mixed with the organopolysiloxane containing Si-bonded hydrogen.

COMPARISON EXAMPLE (A)

The procedure described in Example 1 is repeated, except that 0.2 g of a 1 percent platinum solution, calculated as elemental platinum of a platinum-divinyltetramethyldisiloxane complex in dimethylpolysiloxane having terminal vinyldimethylsiloxy groups is substituted for 2 g of the platinum complex prepared in accordance with (a) above. This solution is prepared in accordance with the following procedure which is described in Example 6 of U.S. Pat. No. 3,814,730.

To a mixture containing 10 parts of $H_2PtCl_6 \cdot 6H_2O$, 20 parts of 1,3-divinyl-1,1,3,3-tetramethyldisiloxane and 50 parts of ethanol, are added 20 parts of sodium bicarbonate. The mixture is boiled under reflux for 30 minutes, then allowed to stand for 15 hours and subsequently filtered. The volatile components are removed from the filtrate by distillation at about 16 mbar. The residue is then dissolved in benzene, filtered and the benzene distilled from the filtrate. The residue is dissolved in a sufficient amount of a dimethylpolysiloxane having terminal vinyldimethylsiloxy groups and a viscosity of 1000 mPa at 23° C. to provide a solution containing 1 percent platinum, calculated as elemental platinum.

The organopolysiloxane platinum complex is stored for 5 days before it is mixed with the organopolysiloxane containing Si-bonded hydrogen. Crosslinking is observed about 2.5 minutes after the two organopolysiloxanes are mixed.

EXAMPLE 3

Mixture A: A mixture containing 102.5 parts of a dimethylpolysiloxane having terminal vinyldimethylsiloxy groups and a viscosity of 22,000 mPa at 23° C., 145 parts of cristoballite meal and 5.5 parts of a commercially available silicon dioxide produced pyrogenically in the gaseous phase with a BET surface area of 200 m²/g which has been treated with dimethyldichlorosilane to impart hydrophobic properties to about 60 percent of its surface area, is mixed with 10 parts of the platinum complex prepared in accordance with the procedure described in (a) above. The resultant mixture contains 40 ppm of platinum, calculated as elemental platinum.

Mixture B: About 97 parts of dimethylpolysiloxane having terminal vinyldimethylsiloxy groups and a viscosity of 22,000 mPa at 23° C., are mixed with 137 parts of cristobalite meal, 9.2 parts of the treated silicon dioxide described in mixture (A) above, and 9.8 parts of a copolymer having a viscosity of 200 mPa at 23° C. and consisting of dimethylsiloxane, methylhydrogensiloxane and trimethylsiloxane units, in which the molar ratio of the dimethylsiloxane units to the methylhydrogensiloxane units is 6:1.

Mixtures (A) and (B) are stored for 3 days at room temperature and then mixed together in a weight ratio of 1:1. Crosslinking is observed 50 seconds after mixtures (A) and (B) are combined at room temperature.

EXAMPLE 4

The procedure described in Example 3 is repeated, except that 10 parts of the platinum complex prepared in accordance with (b) above are substituted for the platinum complex prepared in (a) above.

Crosslinking is observed 30 seconds after mixture (B) is combined with mixture (A) at room temperature.

What is claimed is:

1. A composition comprising an organosilicon compound containing Si-bonded hydrogen and an organic compound containing an aliphatic multiple bond and a platinum catalyst selected from the group consisting of complexes of the formula $(R^1)PtX_2$, and $(R_2SO)(Z)PtY_2$ where R is selected from the group consisting of hydrocarbon radicals and substituted hydrocarbon radicals, $R^1$ is selected from the group consisting of cyclic hydrocarbon radicals and substituted cyclic hydrocarbon radicals having two aliphatic carbon-carbon double bonds, X is selected from the group consisting of halogen atoms and alkyl radicals, Z is a hydrocarbon radical having a carbon-carbon double bond and Y is a halogen atom.

2. The composition of claim 1, wherein $R^1$ is dicyclopentadiene and X is chlorine.

3. The composition of claim 1, wherein $R^1$ is dicyclopentadiene and X is an alkyl radical having from 1 to 4 carbon atoms.

4. The composition of claim 1, wherein the platinum complex having the formula $(R_2SO)(Z)PtY_2$ is dimethylsulfoxide-ethylene-platinum-(II)-dichloride.

5. An improved process for the addition of an organosilicon compound containing Si-bonded hydrogen to an organic compound containing an aliphatic multiple bond in the presence of a platinum catalyst, the improvement which comprises conducting the addition in the presence of a platinum catalyst selected from the group consisting of complexes of the formula $(R^1)PtX_2$, and $(R_2SO)(Z)PtY_2$ where R is selected from the group consisting of hydrocarbon radicals and substituted hydrocarbon radicals, $R^1$ is selected from the group consisting of cyclic hydrocarbon radicals and substituted cyclic hydrocarbon radicals having two aliphatic carbon-carbon double bonds, X is selected from the group consisting of halogen atoms and alkyl radicals, Z is a hydrocarbon radical having a carbon-carbon double bond and Y is a halogen atom.

6. The improved process of claim 5, wherein $R^1$ is dicyclopentadiene and X is chlorine.

7. The improved process of claim 5, wherein $R^1$ is dicyclopentadiene and X is an alkyl radical having from 1 to 4 carbon atoms.

8. The improved process of claim 5, wherein the platinum complex having the formula $(R_2SO)(Z)PtY_2$ is dimethylsulfoxide-ethylene-platinum-(II)-dichloride.

9. The improved process of claims 5, 6, 7, or 8 wherein the organosilicon compound is an organopolysiloxane containing Si-bonded hydrogen and the organic compound is an organopolysiloxane containing alkenyl groups.

10. An improved method for making dental impressions which comprises applying a composition containing an organopolysiloxane having alkenyl groups, an organopolysiloxane containing Si-bonded hydrogen and a platinum catalyst to a tooth and thereafter removing the crosslinked organopolysiloxane impression, the improvement which comprises adding a platinum catalyst selected from the group consisting of complexes of the formula $(R^1)PtX_2$ and $(R_2SO)(Z)PtY_2$ where R is selected from the group consisting of hydrocarbon radicals and substituted hydrocarbon radicals, $R^1$ is selected from the group consisting of cyclic hydrocarbon radicals and substituted cyclic hydrocarbon radicals having two aliphatic carbon-carbon double bonds, X is selected from the group consisting of halogen atoms and alkyl radicals, Z is a hydrocarbon radical having a carbon-carbon double bond and Y is a halogen atom.

* * * * *